United States Patent
Gall et al.

(10) Patent No.: US 12,428,388 B2
(45) Date of Patent: Sep. 30, 2025

(54) NONIONIC POLYETHER SURFACTANTS

(71) Applicant: Cepheid, Sunnyvale, CA (US)

(72) Inventors: Alexander A. Gall, Bothell, WA (US); Ivan Baraznenok, Bothell, WA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 18/754,049

(22) Filed: Jun. 25, 2024

(65) Prior Publication Data

US 2024/0343700 A1   Oct. 17, 2024

Related U.S. Application Data

(62) Division of application No. 17/374,509, filed on Jul. 13, 2021, now abandoned.

(60) Provisional application No. 63/053,426, filed on Jul. 17, 2020.

(51) Int. Cl.
*C07D 307/20* (2006.01)
*C11D 1/72* (2006.01)

(52) U.S. Cl.
CPC .............. *C07D 307/20* (2013.01); *C11D 1/72* (2013.01)

(58) Field of Classification Search
CPC ................................ C07D 307/20; C11D 1/72
See application file for complete search history.

(56) References Cited

U.S. PATENT DOCUMENTS

2007/0295241 A1   12/2007   Park

FOREIGN PATENT DOCUMENTS

| EP | 0 736 591 A2 | 10/1996 | |
|---|---|---|---|
| WO | 2012/148530 A1 | 11/2012 | |
| WO | WO-2013010747 A1 * | 1/2013 | ............ C07C 41/01 |

OTHER PUBLICATIONS

Dannecker, Patrick-Kurt, et al. "Renewable Polyethers via Gabr3-catalyzed Reduction of Polyesters." Angewandte Chemie International Edition, vol. 57, No. 28, Jul. 2018, pp. 8775-8779. DOI.org (Crossref), https://doi.org/10.1002/anie.201804368. (Year: 2018).*
Dwivedi, M, et al., "Polysorbate degradation in biotherapeutic formulations: Identification and discussion of current root causes," International Journal of Pharmaceutics 552(1):422-436, 2018.
Gozlan, Charlotte, et al., "Preparation of amphiphilic sorbitan monoethers through hydrogenolysis of sorbitan acetals and evaluation as bio-based surfactants," Green Chemistry 18(7):1994-2004, 2016.
International Search Report and Written Opinion mailed Sep. 24, 2021, issued in corresponding International Application No. PCT/US2021/041421, filed Jul. 13, 2021, 15 pages.
Mao, Z., et al., "Catalytic Hydrosilylation of Organic Esters Using Manganese Carbonyl Acetyl Complexes, (L)(CO) 4MnC(O)CH3 (L=CO, PPh3)," J. Am. Chem. Soc. 117:10139-10140, 1995.
Sakai, N., et al., "An Efficient One-Pot Synthesis of Unsymmetrical Ethers: A Directly Reductive Deoxygenation of Esters Using an InBr3/Et3SiH Catalytic System," J. Org. Chem. 72(15):5920-5922, 2007.
Yato M., et al., "Reduction of carboxylic esters to ethers with triethyl silane in the combined use of titanium tetrachloride and trimethylsilyl trifluoromethanesulfonate," Tetrahedron 57(25):5353-5359, 2001.
Biermann, U., and J.O. Metzger, "Synthesis of Ethers by GaBr3-Catalyzed Reduction of Carboxylic Acid Esters and Lactones by Siloxanes," ChemSusChem 7:644-649, 2014.
Mahmood, M.E., and D.A.F. Al-Koofee, "Effect of Temperature Changes on Critical Micelle Concentration for Tween Series Surfactant," Global Journal of Science Frontier Research Chemistry 13(4), 2013.
Office Application mailed Mar. 20, 2023, from U.S. Appl. No. 17/374,509, filed Jul. 13, 2021, 15 pages.
Office Application mailed Mar. 27, 2024, from U.S. Appl. No. 17/374,509, filed Jul. 13, 2021, 13 pages.
Final Office Application mailed Aug. 28, 2023, from U.S. Appl. No. 17/374,509, filed Jul. 13, 2021, 11 pages.

* cited by examiner

*Primary Examiner* — Clinton A Brooks
*Assistant Examiner* — Kyle Nottingham
(74) *Attorney, Agent, or Firm* — McAndrews, Held & Malloy, Ltd.

(57) ABSTRACT

Non-ionic polyether surfactants with improved resistance to hydrolysis are provided.

14 Claims, 4 Drawing Sheets

NONIONIC POLYETHER SURFACTANTS

CROSS-REFERENCE TO RELATED APPLICATIONS

This application is a division of U.S. application Ser. No. 17/374,509, filed Jul. 13, 2021, which claims the benefit of U.S. Application No. 63/053,426, filed Jul. 17, 2020, each expressly incorporated herein by reference in its entirety.

BACKGROUND

Polysorbates are amphiphilic, nonionic surfactants comprising fatty acid esters of polyoxyethylene sorbitan. Polysorbates are widely as research reagents and in protein pharmaceuticals to stabilize the proteins against interface-induced aggregation and to minimize surface adsorption of proteins. The main disadvantage of polysorbates is their susceptibility to hydrolysis due to the presence of an ester bond. Acid- and base-promoted hydrolytic degradation as well as enzymatic degradation of polysorbates is well-documented, limiting their use in applications that require basic or acidic pH conditions.

Thus, a need exists for a nonionic surfactant that would not be easily hydrolysable

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a compound of Formula (I):

an isomer, a hydrate, a solvate, or a tautomer thereof, wherein:

R is a an optionally substituted C6-C70 alkyl or optionally substituted C6-C70 alkenyl;
w is an integer ranging from 0 to 20,
x is an integer ranging from 0 to 20,
y is an integer ranging from 0 to 20, and
z is an integer ranging from 0 to 20.

In some embodiments, R is an unsubstituted C6-C70 alkyl or unsubstituted C6-C70 alkenyl. In certain embodiments, R is an unsubstituted C10-C25 alkyl or unsubstituted C10-C25 alkenyl. In certain embodiments, the sum of w, x, y, and z is 20.

In some embodiments, the compound is represented by Formula (IA):

an isomer, a hydrate, a solvate, or a tautomer thereof, wherein R, w, x, y, and z are as defined for compound of Formula (I).

In some embodiments of Formula (I) or Formula (IA), R is n-decyl, n-undecyl, n-dodecyl, n-hexadecyl, or n-heptadecyl.

In another aspect, the disclosure provides a method of preparing a compound of Formula (I):

an isomer, a hydrate, a solvate, or a tautomer thereof, wherein:

R is a an optionally substituted C6-C70 alkyl or optionally substituted C6-C70 alkenyl;
w is an integer ranging from 0 to 20,
x is an integer ranging from 0 to 20,
y is an integer ranging from 0 to 20, and
z is an integer ranging from 1 to 20,
comprising the steps of:
forming a trimethylsilyl protected derivative of compound of formula (II):

and
(b) contacting the trimethylsilyl derivative of compound of formula (II) with a suitable reducing agent and gallium tribromide.

In some embodiments, forming a trimethylsilyl derivative of compound of Formula (II) is done by contacting a compound of Formula (II) with a silylating agent in a suitable solvent. In some embodiments, the silylating agent is hexamethyldisilazane (HMDS). In some embodiments, the reducing agent is 1,1,3,3-tetramethyldisiloxane.

In some embodiments, step (b) is performed at a temperature ranging from about 25° C. to about 80° C. In certain embodiments, step (b) is performed at a room temperature. In some embodiments, step (b) does not require a solvent.

In some embodiments, the method further comprises contacting the product of step (b) with water.

In a third aspect, provided herein is a surfactant composition comprising a compound of Formula (I) or (IA).

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The disclosure provides polysorbate ether compounds that can be useful as nonionic surfactants in applications where nonionic surfactants such as polysorbate 20 or polysorbate 80 are employed. Thus, in one aspect, provided herein is a compound represented by Formula (I):

(I)

or an isomer, a hydrate, a solvate, or a tautomer thereof, wherein:
R is an optionally substituted C6-C70 alkyl or optionally substituted C6-C70 alkenyl;
w is an integer ranging from 0 to 20,
x is an integer ranging from 0 to 20,
y is an integer ranging from 0 to 20, and
z is an integer ranging from 0 to 20.

In some embodiments of Formula (I), R is an unsubstituted C6-C50 alkyl. In other embodiments, R is an unsubstituted C10-C25 alkyl.

In certain embodiments, the sum of w, x, y, and z is 20.

In some embodiments, the compound is represented by Formula (IA):

(IA)

or an isomer, a hydrate, a solvate, or a tautomer thereof,
wherein R, w, x, y, and z are as defined above for Formula (I).

In some embodiments, R is n-decyl, n-undecyl, n-dodecyl, n-hexadecyl, or n-heptadecyl.

In some embodiments, the compound is Compound 1:

or an isomer, solvate, hydrate, or a tautomer thereof,
wherein x+y+x=20.

In some embodiments, the compound is Compound 2:

or an isomer, solvate, hydrate, or a tautomer thereof,
wherein x+y+x=20.

As used herein, the terms "alkyl," and "alkenyl" include straight-chain, branched-chain, and cyclic monovalent hydrocarbyl radicals, and combinations of these, which contain only C and H when they are unsubstituted. The total number of carbon atoms in each such group is sometimes described herein, e.g., when the group can contain up to ten carbon atoms it can be represented as 1-10C, as $C_1$-$C_{10}$, C—C10, or C1-10.

Alkyl and alkenyl groups can be optionally substituted to the extent that such substitution makes sense chemically.

Typical substituents include, but are not limited to, halogens (F, Cl, Br, I), =O, =N—CN, =N—OR, =NR, OR, NR$_2$, SR, SO$_2$R, SO$_2$NR$_2$, NRSO$_2$R, NRCONR$_2$, NRC(O)OR, NRC(O)R, CN, C(O)OR, C(O)NR$_2$, OC(O)R, C(O)R, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halogens (F, Cl, Br, I), =O, =N—CN, =N—OR', =NR', OR', NR'$_2$, SR', SO$_2$R', SO$_2$NR'$_2$, NR'SO$_2$R', NR'CONR'$_2$, NR'C(O)OR', NR'C(O) R', CN, C(O)OR', C(O)NR'$_2$, OC(O)R', C(O)R', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl and alkenyl groups can also be substituted by C1-C8 acyl, C2-C8 heteroacyl,

C6-C10 aryl or C5-C10 heteroaryl, each of which can be substituted by the substituents that are appropriate for the particular group.

"Optionally substituted," as used herein, indicates that the particular group being described may have one or more hydrogen substituents replaced by a non-hydrogen substituent. In some optionally substituted groups or moieties, all hydrogen substituents are replaced by a non-hydrogen substituent, e.g., C1-C6 alkyl, C2-C6 heteroalkyl, alkynyl, halogens (F, Cl, Br, I), N$_3$, OR, NR$_2$, SR, SO$_2$R, SO$_2$NR$_2$, NRSO$_2$R, NRCONR$_2$, NRC(O)OR, NRC(O)R, CN, C(O) OR, C(O)NR$_2$, OC(O)R, C(O)R, oxo, and NO$_2$, wherein each R is independently H, C1-C6 alkyl, or C2-C6 heteroalkyl. Where an optional substituent is attached via a double bond, such as a carbonyl oxygen or oxo (=O), the group takes up two available valences, so the total number of substituents that may be included is reduced according to the number of available valences.

Isomers, e.g., stereoisomers, and tautomers of the compounds disclosed herein are also within the scope of this disclosure. As used herein, "stereoisomer" or "stereoisomers" refer to compounds that differ in the chirality of one or more stereocenters. Stereoisomers include enantiomers and diastereomers. As used herein, "tautomer" refers to alternate forms of a compound that differ in the position of a proton, such as enol-keto and imine-enamine tautomers.

In another aspect, provided herein is a nonionic surfactant composition comprising one or more compounds of Formula (I) or Formula (IA).

In yet another aspect, the disclosure provides a method of synthesis of a compound of Formula (I), comprising the steps of contacting a protected derivative of a compound of Formula (II):

(II)

or an isomer, a hydrate, a solvate, or a tautomer thereof, wherein:

R is an optionally substituted C6-C70 alkyl or optionally substituted C6-C70 alkenyl;

w is an integer ranging from 0 to 20, x is an integer ranging from 0 to 20, y is an integer ranging from 0 to 20, and z is an integer ranging from 0 to 20, with a suitable reducing agent thereby reducing the ester group of the compound of Formula (II) to the corresponding ether group.

In certain embodiments, the compounds disclosed herein are prepared by reduction of a polysorbate compound with a suitable reducing agent, for example, 1,1,3,3-tetramethyldisiloxane in the presence of gallium tribromide.

In some embodiments, the synthesis of a compound of Formula (I) is performed according to the synthetic route depicted in Scheme 1.

Scheme 1

In some embodiments, the methods disclosed herein comprise forming a trimethylsilyl protected derivative of compound of Formula (II) and contacting the trimethylsilyl derivative of compound of Formula (II) with a suitable reducing agent and gallium tribromide.

In some embodiments, contacting the trimethylsilyl derivative of compound of formula (II) with a suitable reducing agent and gallium tribromide is done in a suitable solvent. Any suitable solvent can be used in the steps described above.

In some embodiments, a trimethylsilyl protected derivative of compound of Formula (II) can be formed by contacting a compound of Formula (II) with a suitable silylating agent. Silylating agents and methods of their use are known in the art. Any suitable silylating agent can be used to form a trimethylsilyl-protected compound of Formula (II). In some embodiments, the silylating agent is hexamethyldisilazane (HMDS).

Any suitable reducing agent can be used to for the reduction the ester group of the compound of Formula (II) to the corresponding ether group. In some embodiments, the reducing agent is 1,1,3,3-tetramethyldisiloxane. In some embodiments, the reduction step involves contacting a protected derivative of compound of Formula (II) with 1,1,3, 3-tetramethyldisiloxane and gallium tribromide. The reduction can be performed at any suitable temperature, for example, at a temperature ranging from about 25° C. to about 80° C. In some embodiments, the reduction step does not require a solvent.

In some embodiments, the methods further include a hydrolysis step, for example the method comprises contacting the product of the reduction step with water, thereby removing the protecting groups (e.g., trimethylsilyl groups).

In some embodiments, the compound of Formula (II) is a polysorbate or polyethyleneglycol sorbitan ester. Examples of suitable polyethyleneglycol sorbitan esters include especially polyoxyethylene sorbitan monolaurate (e.g., polysorbate 20 or Tween 20®), polyoxyethylene sorbitan monooleate (e.g., polysorbate 80 or Tween 80®), polyoxyethylene sorbitan monolaurate, polyoxyethylene sorbitan monoelaidate, polyoxyethylene sorbitan monomyristoleate, and polyoxyethylene sorbitan monopalmitate.

As used herein, the term "about" indicates that the subject value can be modified by plus or minus 5% and still fall within the disclosed embodiment.

While each of the elements of the present disclosure is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference.

While illustrative embodiments have been illustrated and described, it will be appreciated that various changes can be made therein without departing from the spirit and scope of the invention.

As can be appreciated from the disclosure above, the present invention has a wide variety of applications. The invention is further illustrated by the following examples, which are only illustrative and are not intended to limit the definition and scope of the invention in any way.

EXAMPLES

Preparation of Exemplary Saturated Polysorbate Ether (Compound 1) as 5% Aqueous Solution Neat dry Tween 20® (11.4 g, 9 mmol) was dissolved in HMDS (23 mL) and THF (46 mL). Ammonium sulfate (0.06 g, 0.45 mmol) was added and mixture was stirred overnight at ambient temperature. The mixture was evaporated in vacuo, co-evaporated twice with 20 mL toluene and dried 1 h under high vacuum, giving 13.4 g of heavy oil. The oil was heated to 50° C., and $GaBr_3$ (310 mg, 1 mmol) was added followed by dropwise addition of 1,1,3,3-tetramethyldisiloxane (5.0 mL, 28 mmol). Mixture was stirred at 60° C. for 8 h, cooled, dissolved in 20 mL toluene and evaporated to dryness. Oily residue was mixed with 30 mL water, stirred 1 h and evaporated to dryness, then co-evaporated with additional 30 mL water. The crude product was dissolved in 200 mL water and filtered via Dowex 50 WX8-400 ion exchange resin (100 g). The filtrate was diluted with water to 220 mL total volume, and the pH of the solution was adjusted to 9-10 using aqueous $NH_3$.

Preparation of Exemplary Saturated Polysorbate Ether (Compound 1)

Neat dry Tween 20® (13.3 g, 11 mmol) was dissolved in HMDS (26 mL) and THF (52 mL). Ammonium sulfate (0.054 g, 0.41 mmol) was added and mixture was stirred overnight at ambient temperature. The mixture was evaporated in vacuo, co-evaporated twice with 25 mL toluene and dried 1 h under high vacuum. The resulting oil was heated to 50° C., and $GaBr_3$ (415 mg, 1.3 mmol) was added followed by dropwise addition of 1,1,3,3-tetramethyldisiloxane (6.9 mL, 39 mmol). The mixture was stirred at 60° C. for 8 h, cooled, dissolved in 26 mL toluene and evaporated to dryness. The oily residue was mixed with 39 mL water, stirred 15 h and evaporated to dryness, then co-evaporated with additional 39 mL water. The crude product was dissolved in 100 mL 5% MeOH in $CH_2Cl_2$ and filtered via 20 g silica. Silica pad was washed with 150 mL 5% MeOH in $CH_2Cl_2$. The filtrate was evaporated to dryness and dissolved in 70 mL water and 70 mL heptane. The aqueous layer was separated, and the organic layer was extracted with 35 mL water. The combined aqueous layers were evaporated giving 11.5 g (88%) of the exemplary polysorbate ether as viscous clear oil.

Preparation of Exemplary Unsaturated Polysorbate Ether (Compound 2)

Compound 2 was prepared from Tween 80® by the procedure described above for the preparation of Compound 1.

Figure 1A:
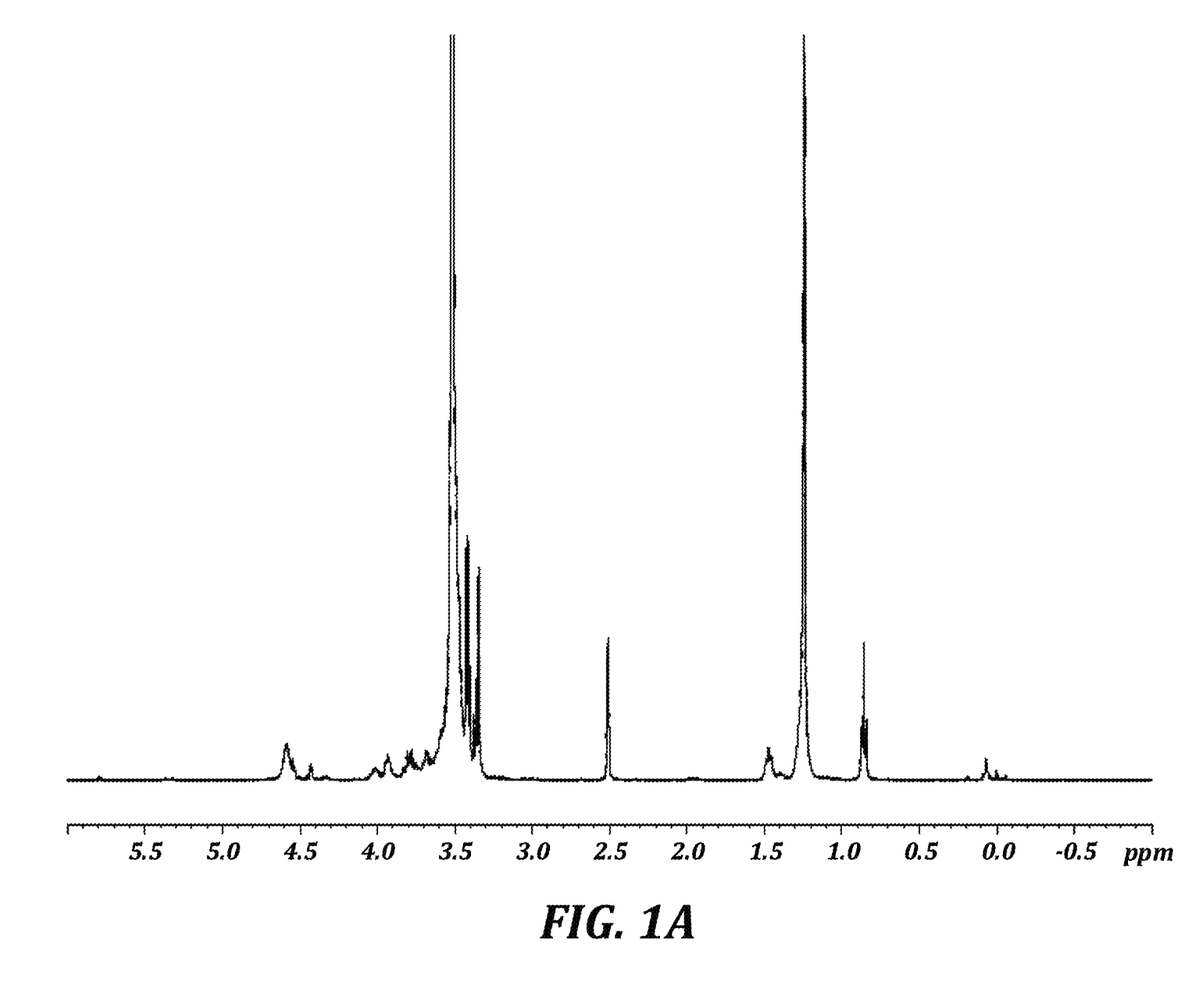
FIG. 1A is an NMR spectrum of Polysorbate 20 (Tween 20®) and FIG. 1B is an NMR spectrum of an exemplary polysorbate ether (Compound 1).
Figure 1B:
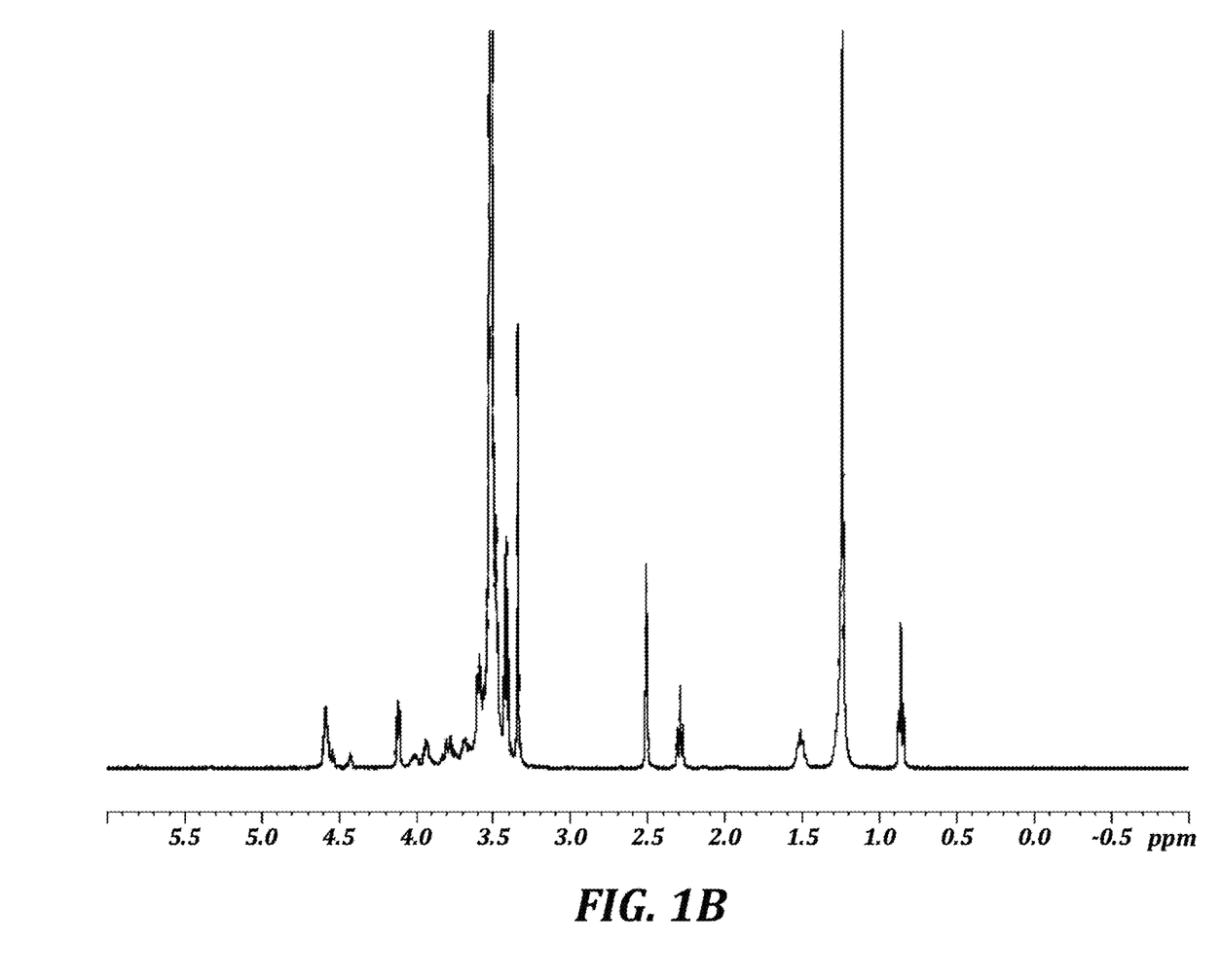
Figure 2A:
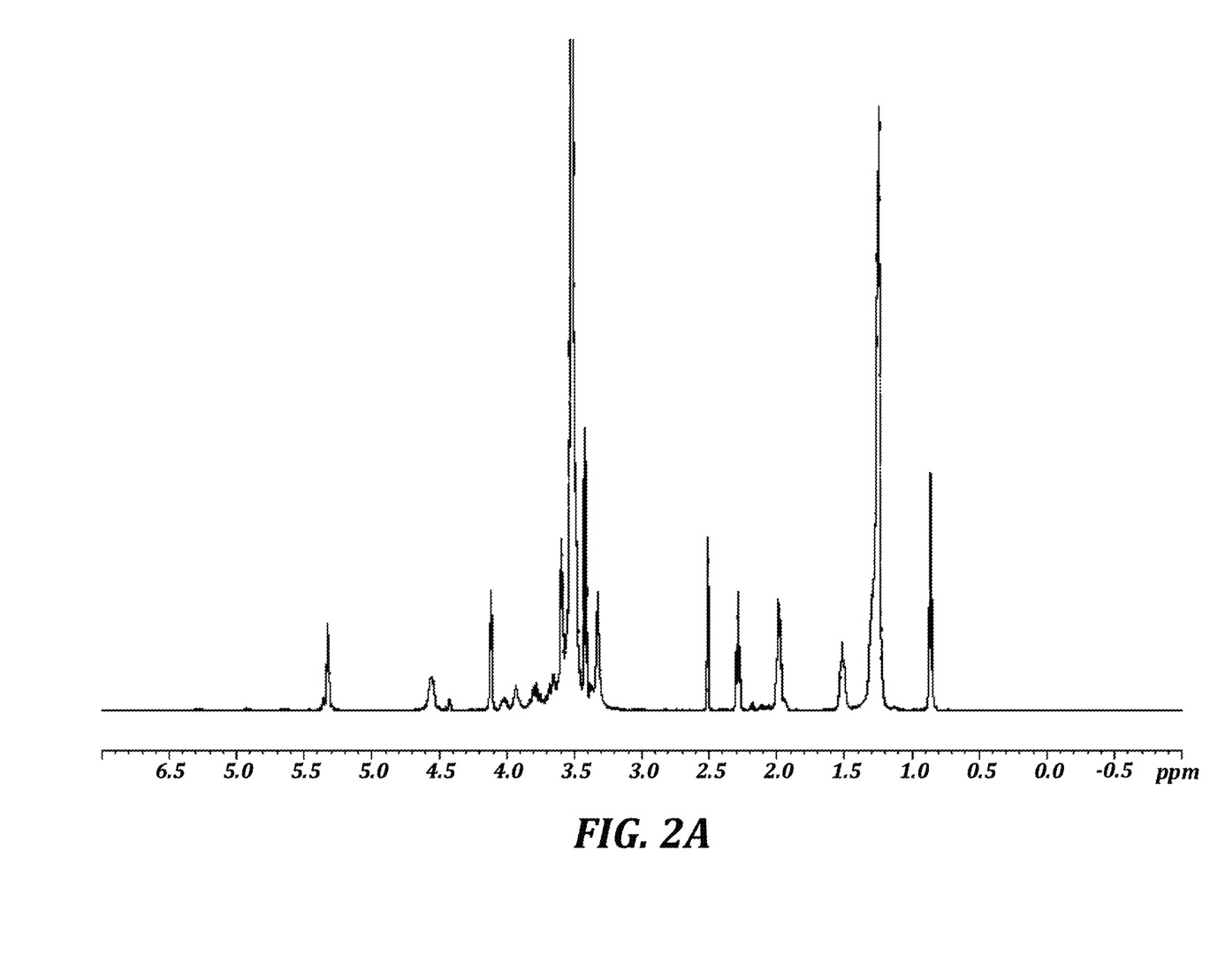
FIG. 2A is an NMR spectrum of Polysorbate 80 (Tween 80®) and FIG. 2B is an NMR spectrum of an exemplary polysorbate ether (Compound 2).
Figure 2B:
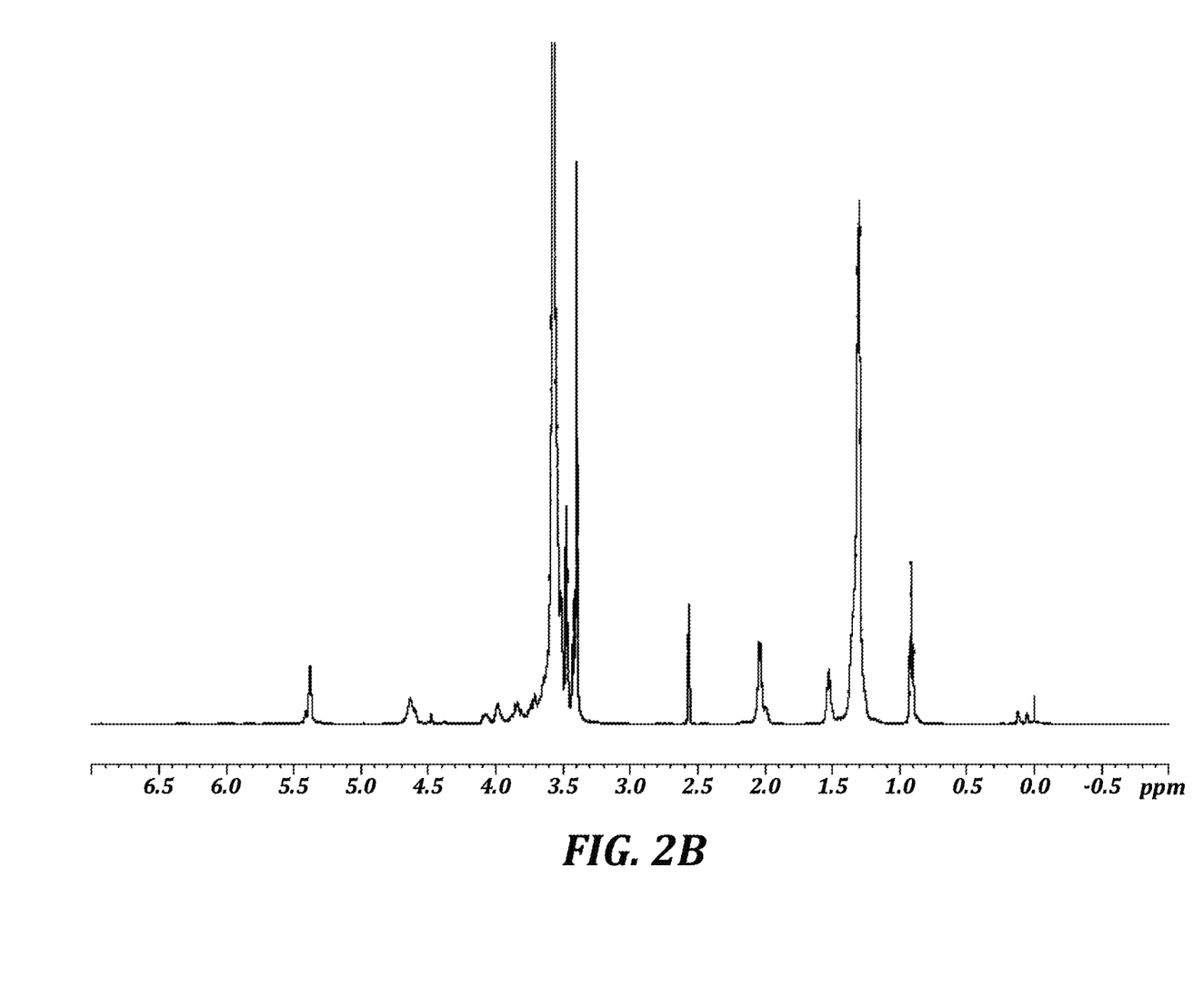

Neat dry Tween 80® (10.6 g, 8 mmol) was dissolved in HMDS (20 mL) and THF (40 mL). Ammonium sulfate (0.05 g, 0.4 mmol) was added, and mixture was stirred overnight at ambient temperature. The mixture was evaporated in vacuo, co-evaporated twice with 20 mL toluene and dried 1 h under high vacuum, giving 12.5 g of heavy oil. The oil was heated to 50° C., and $GaBr_3$ (360 mg, 1.2 mmol) was added followed by dropwise addition of 1,1,3,3-tetramethyldisiloxane (5.0 mL, 28 mmol). The mixture was stirred at 60° C. for 8 h, cooled, dissolved in 20 mL toluene and evaporated to dryness. Oily residue was mixed with 30 mL water, stirred 1 h and evaporated to dryness, then co-evaporated with additional 30 mL water. Crude product was dissolved in 150 mL water and filtered via Dowex 50 WX8-400 ion exchange resin (50 g). Filtrate was diluted with water to 200 mL total volume, pH of the solution was adjusted to 9-10 using aqueous $NH_3$. A small sample was evaporated for 1H NMR analysis (FIG. 2).

Stability of Exemplary Polysorbate Ethers

In the following experiments, the properties of exemplary reduced polysorbates were compared with the starting materials purchased from Sigma: Tween 20® BioXtra, Cat No P7949 and Tween 80® BioXtra, Cat No P8074

Stability in 2M NaOH

The following solutions are prepared in two vials: (A) 1% Tween 20® in 2M NaOH; (B) 1% Compound 2 in 2M NaOH. Both solutions were left at room temperature and the changes were observed visually. The solution A (initially clear) became non-transparent within one hour and turned into stiff gel the next day due to precipitation of the fatty acid salt. Solution B remained clear for at least one month.

Similarly, hydrolytic stability of (A) Tween 80® and (B) Compound 2 were compared. The solution A became cloudy within one hour and turned into a stiff gel the next day due to precipitation of the fatty acid salt. Solution B remained clear for at least one month.

Enzymatic Stability

Stability of surfactants in the presence of hydrolyzing enzymes was tested according to a simplified literature procedure (Francisco J. Plou, Manuel Ferrer, Oscar M. Nuero, Maria V. Calvo, Miguel Alcalde, Fuensanta Reyes, Antonio Ballesteros. Analysis of Tween 80 as an esterase/lipase substrate for lipolytic activity assay. *Biotechnology Techniques*, Vol 12, No 3, March 1998, pp. 183-186.)

B1. Resistance to Lipase Hydrolysis

The following solutions are prepared in two vials: (A) to 20 mL of 1% Tween 20® in 10 mM tris-HCl (pH 8.0) is added 1 mL of 5% CaCl$_2$) followed by 2 mL of 2 mg/mL solution of Lipase from porcine pancreas (Sigma L3126) in 10 µM tris-HCl (pH 8.0); (B) to 20 mL of 1% Compound 1 in 10 mM tris-HCl (pH 8.0) is added 1 mL of 5% CaCl$_2$) followed by 2 mL of 2 mg/mL solution of Lipase from porcine pancreas (Sigma L3126) in 10 µM tris-HCl (pH 8.0). Both solutions were left at room temperature, and changes were observed visually. The solution A became cloudy within one hour and became non-transparent the next day due to precipitation the calcium salt of the fatty acid. Solution B remained clear for at least one month.

Tween 80® and Compound 2 demonstrated similar differences in stability when subjected to Lipase hydrolysis conditions as described above.

B2. Resistance to Esterase Hydrolysis

The following solutions were prepared in two vials: (A) to 20 mL of 1% Tween 20® in 10 mM tris-HCl (pH 8.0) is added 1 mL of 5% CaCl$_2$) followed by 40 µL of 100 UN/mL solution of Esterase from porcine liver (Sigma E2884) in 10 µM tris-HCl (pH 8.0); (B) to 20 mL of 1% Compound 1 in 10 mM tris-HCl (pH 8.0) is added 1 mL of 5% CaCl2 followed by 40 µL of 100 UN/mL solution of Esterase from porcine liver in 10 µM tris-HCl (pH 8.0). Both solutions were left at room temperature and changes were observed visually. The solution A became cloudy within one hour and became non-transparent the next day due to precipitation the calcium salt of the fatty acid. Solution B remained clear for at least one month.

Tween 80® and Compound 2 demonstrated similar differences in stability when subjected to Esterase hydrolysis conditions as described above.

While illustrative embodiments have been illustrated and described, it will be appreciated that various changes can be made therein without departing from the spirit and scope of the invention.

The invention claimed is:

1. A method of preparing of a compound of Formula (I):

(I)

or a stereoisomer, a hydrate, or a solvate thereof, wherein:
R is an optionally substituted $C_6$-$C_{70}$ alkyl or optionally substituted $C_6$-$C_{70}$ alkenyl;
w is an integer ranging from 0 to 20,
x is an integer ranging from 0 to 20,
y is an integer ranging from 0 to 20, and
z is an integer ranging from 1 to 20,
comprising the steps of:
(a) forming a trimethylsilyl protected derivative of a compound of formula (II):

(II)

and
(b) contacting the trimethylsilyl protected derivative of the compound of formula (II) with a reducing agent and gallium tribromide, optionally in a solvent.

2. The method of claim 1, wherein forming a trimethylsilyl derivative of compound of Formula (II) is done by contacting a compound of Formula (II) with a silylating agent in a solvent.

3. The method of claim 1, wherein the silylating agent is hexamethyldisilazane (HMDS).

4. The method of claim 1, wherein the reducing agent is 1,1,3,3-tetramethyldisiloxane.

5. The method of claim 1, wherein step (b) is performed at a temperature ranging from about 25° C. to about 80° C.

6. The method of claim 1, wherein step (b) does not require a solvent.

7. The method of claim 1, further comprising contacting the product of step (b) with water.

8. The method of claim 1, wherein R is an unsubstituted $C_6$-$C_{50}$ alkyl or unsubstituted $C_6$-$C_{50}$ alkenyl.

9. The method of claim 1, wherein R is an unsubstituted $C_{10}$-$C_{25}$ alkyl or unsubstituted $C_{10}$-$C_{25}$ alkenyl.

10. The method of claim 1, wherein the sum of w, x, y, and z is 20.

11. The method of claim 1, wherein the compound is represented by Formula (IA):

(IA)

or a stereoisomer, a hydrate, or a solvate thereof.

12. The method of claim 1, wherein R is n-decyl, n-undecyl, n-dodecyl, n-hexadecyl, or n-heptadecyl.

13. The method of claim 1, wherein the compound is:

or an stereoisomer, solvate, or hydrate thereof, wherein w+x+y+z=20.

14. The method of claim 1, wherein the compound of Formula (I) is or a stereoisomer, solvate, or hydrate thereof, wherein w+x+y+z=20.

* * * * *